(12) United States Patent
Ramirez et al.

(10) Patent No.: US 7,687,650 B2
(45) Date of Patent: Mar. 30, 2010

(54) CHEMICAL COMPOSITIONS AND METHODS OF MAKING THEM

(75) Inventors: Jose E. Ramirez, Trumbull, CT (US); Joseph Faryniarz, Middlebury, CT (US)

(73) Assignee: JR Chem, LLC, Key West, FL (US)

( * ) Notice: Subject to any disclaimer, the term of this patent is extended or adjusted under 35 U.S.C. 154(b) by 70 days.

(21) Appl. No.: 11/647,623

(22) Filed: Dec. 29, 2006

(65) Prior Publication Data

US 2007/0191620 A1 Aug. 16, 2007

Related U.S. Application Data

(60) Provisional application No. 60/764,968, filed on Feb. 3, 2006.

(51) Int. Cl.
C07F 1/00 (2006.01)
(52) U.S. Cl. ..................................................... 556/114
(58) Field of Classification Search .................. 556/114
See application file for complete search history.

(56) References Cited

U.S. PATENT DOCUMENTS

| | | |
|---|---|---|
| 46,494 A | 2/1865 | Pike |
| 51,868 A | 1/1866 | Schuster |
| 55,889 A | 6/1866 | Noll |
| 81,008 A | 8/1868 | Roemheld |
| 81,711 A | 9/1868 | Van Wagenen |
| 87,343 A | 3/1869 | Johnson |
| 88,973 A | 4/1869 | McDowell |
| 92,065 A | 6/1869 | Lighthall |
| 93,300 A | 8/1869 | Hall et al. |
| 116,875 A | 7/1871 | Shannon |
| 124,751 A | 3/1872 | Lauer |
| 127,925 A | 6/1872 | Roskopf |
| 128,385 A | 6/1872 | Goffinet |
| 145,749 A | 6/1873 | Pawlewski et al. |
| 140,768 A | 7/1873 | Fisher |
| 143,133 A | 9/1873 | Fehr |
| 149,857 A | 1/1874 | Halpen |
| 171,875 A | 1/1876 | Sievers |
| 173,607 A | 2/1876 | Fehr |
| 209,331 A | 6/1878 | Littleton |
| 229,014 A | 6/1880 | Sharetts |
| 232,807 A | 10/1880 | Dennett |
| 238,015 A | 2/1881 | Yater |
| 264,783 A | 9/1882 | Squier |
| 277,221 A | 5/1883 | Buse |
| 284,335 A | 9/1883 | Scott |
| 318,468 A | 5/1885 | Haley |
| 320,836 A | 6/1885 | Bisaillon |
| 411,657 A | 9/1889 | Grosbety |
| 415,208 A | 11/1889 | Johson |
| 430,048 A | 6/1890 | Wainwright |
| 432,611 A | 7/1890 | Hall |
| 627,296 A | 6/1899 | Camnitzer |
| 928,539 A | 7/1909 | Pucciarelli |
| 944,738 A | 12/1909 | Loose |
| 992,937 A | 5/1911 | Brodbeck et al. |
| 1,059,841 A | 4/1913 | Crookes |
| 1,086,900 A | 2/1914 | David |
| 1,332,190 A | 2/1920 | Hull |
| 1,411,577 A | 4/1922 | Mullins et al. |
| 1,488,097 A | 3/1924 | Creger |
| 1,584,173 A | 5/1926 | Holzapfel |
| 1,593,485 A | 7/1926 | Crosnier |
| 1,627,963 A | 5/1927 | Fuller |
| 1,809,082 A | 6/1931 | Urkov et al. |
| 1,908,176 A | 5/1933 | Osterberg |
| 1,947,568 A | 2/1934 | Noonan |
| 1,949,797 A | 3/1934 | Kaufmann |
| 1,982,148 A | 11/1934 | Zimbron, Jr. |
| 2,002,829 A | 5/1935 | Osterberg |
| 2,054,989 A | 9/1936 | Moore |
| 2,087,162 A | 7/1937 | Moore |
| 2,095,092 A | 10/1937 | Barton |
| 2,114,490 A | 4/1938 | Harris |
| 2,129,836 A | 9/1938 | Goodman |
| 2,153,653 A | 4/1939 | Stux |

(Continued)

FOREIGN PATENT DOCUMENTS

WO     WO 94/15216     7/1994

(Continued)

OTHER PUBLICATIONS

Ruiz-Pérez, et al.. "Malonic Acid: a multi-modal bridging ligand for new architectures and properties on molecule-based magnets" *Polyhedron* 2003, accepted.

(Continued)

*Primary Examiner*—Deborah D Carr
(74) *Attorney, Agent, or Firm*—Carter, DeLuca, Farrell & Schmidt, LLP

(57) ABSTRACT

Metal complex salts of the coordination elements listed in Groups IIIA to VIIIA, Groups IB to IIIB, of periods 4 and 5 and aluminum in Group IIIB, period 3 of The Periodic Table of the Elements, obtained as the reaction products of polyfunctional acids with two or more of such elements are described. Copper-zinc malonates and a process for their preparation are disclosed.

7 Claims, No Drawings

U.S. PATENT DOCUMENTS

| | | | |
|---|---|---|---|
| 2,194,218 A | 3/1940 | Thurstan |
| 2,223,142 A | 11/1940 | Weirich |
| 2,241,331 A | 5/1941 | Shelton |
| 2,254,636 A | 9/1941 | Vangunten |
| 2,267,739 A | 12/1941 | Kemppe |
| 2,289,125 A | 7/1942 | Keil |
| 2,299,604 A | 10/1942 | Weirich |
| 2,344,830 A | 3/1944 | Mohs |
| 2,361,161 A | 10/1944 | Anderson |
| 2,370,561 A | 2/1945 | Mecca |
| 2,372,807 A | 4/1945 | Brown |
| 2,420,271 A | 5/1947 | Travis et al. |
| 2,420,389 A | 5/1947 | Travis et al. |
| 2,469,228 A | 5/1949 | Gertler |
| 2,527,686 A | 10/1950 | Sandberg |
| 2,556,567 A | 6/1951 | Wright |
| 2,602,039 A | 8/1952 | Wershaw |
| 2,649,398 A | 8/1953 | Wright et al. |
| 2,652,355 A | 9/1953 | Ercoli et al. |
| 2,673,364 A | 3/1954 | Diveley |
| 2,703,777 A | 3/1955 | Feinstein et al. |
| 2,736,681 A | 2/1956 | Tishler |
| 2,748,781 A | 6/1956 | Collat |
| 2,838,440 A | 6/1958 | Thurmon |
| 2,843,522 A | 7/1958 | Mahon |
| 2,846,322 A | 8/1958 | Buchalter |
| 2,870,150 A | 1/1959 | Wright et al. |
| 2,870,151 A | 1/1959 | Wright et al. |
| 2,872,372 A | 2/1959 | Hull |
| 2,991,224 A | 7/1961 | Bell |
| 3,013,883 A | 12/1961 | Welcker et al. |
| 3,033,755 A | 5/1962 | Jacobi |
| 3,035,988 A | 5/1962 | Cohen |
| 3,084,105 A | 4/1963 | Slodki |
| 3,137,622 A | 6/1964 | Mueller et al. |
| 3,146,168 A | 8/1964 | Battista |
| 3,164,523 A | 1/1965 | Fox et al. |
| 3,184,376 A | 5/1965 | Degoli |
| 3,210,248 A | 10/1965 | Feldmann et al. |
| 3,215,599 A | 11/1965 | Thau et al. |
| 3,255,079 A | 6/1966 | Schroeder et al. |
| 3,290,218 A | 12/1966 | de Jong |
| 3,317,372 A | 5/1967 | Hart |
| 3,366,114 A | 1/1968 | Kanter |
| 3,590,123 A | 6/1971 | Melloh et al. |
| 3,749,772 A | 7/1973 | Cardarelli et al. |
| 3,821,370 A | 6/1974 | Tenta |
| 3,821,371 A | 6/1974 | Battista |
| 3,826,845 A | 7/1974 | Suyama et al. |
| 3,856,941 A | 12/1974 | Turner |
| 3,896,238 A | 7/1975 | Smith |
| 3,903,268 A | 9/1975 | Balassa |
| 3,949,072 A | 4/1976 | Tenta |
| 4,048,300 A | 9/1977 | Tomlinson et al. |
| 4,100,269 A | 7/1978 | Pader |
| 4,138,477 A | 2/1979 | Gaffar |
| 4,146,607 A | 3/1979 | Ritchey |
| 4,154,911 A | 5/1979 | Bak et al. |
| 4,160,821 A | 7/1979 | Sipos |
| 4,161,526 A | 7/1979 | Gorman |
| 4,166,108 A | 8/1979 | Brown et al. |
| 4,226,851 A | 10/1980 | Sompayrac |
| 4,226,889 A | 10/1980 | Yuhas |
| 4,229,430 A | 10/1980 | Fahim et al. |
| 4,229,437 A | 10/1980 | Likens et al. |
| 4,255,418 A | 3/1981 | Bailey |
| 4,273,763 A | 6/1981 | Horrobin |
| 4,285,967 A | 8/1981 | Gubernick et al. |
| 4,291,025 A | 9/1981 | Pellico |
| 4,298,601 A | 11/1981 | Howard |
| 4,302,447 A | 11/1981 | Horrobin |
| 4,305,842 A | 12/1981 | Asakawa et al. |
| 4,309,989 A | 1/1982 | Fahim |
| 4,310,516 A | 1/1982 | Chang et al. |
| 4,315,916 A | 2/1982 | Likens et al. |
| 4,322,400 A | 3/1982 | Yuhas |
| 4,330,527 A | 5/1982 | Arima et al. |
| 4,331,653 A | 5/1982 | Brown et al. |
| 4,335,110 A | 6/1982 | Collins |
| 4,349,536 A | 9/1982 | Hausler |
| 4,372,296 A | 2/1983 | Fahim |
| 4,375,968 A | 3/1983 | Manhart |
| 4,376,115 A | 3/1983 | McCrorey |
| 4,395,398 A | 7/1983 | Yamamoto |
| 4,406,881 A | 9/1983 | Ladanyi |
| 4,428,933 A | 1/1984 | King |
| 4,430,324 A | 2/1984 | Viccaro |
| 4,444,755 A | 4/1984 | Horrobin |
| 4,465,666 A | 8/1984 | Lukas et al. |
| 4,469,684 A | 9/1984 | Huggins et al. |
| 4,477,439 A | 10/1984 | D'Alelio |
| 4,486,488 A | 12/1984 | Pietsch et al. |
| 4,503,037 A | 3/1985 | Szijjarto et al. |
| 4,512,978 A | 4/1985 | Inwood |
| 4,515,779 A | 5/1985 | Elliott |
| 4,522,806 A | 6/1985 | Muhlemann et al. |
| 4,568,540 A | 2/1986 | Asano et al. |
| 4,604,234 A | 8/1986 | Fujii et al. |
| 4,606,920 A | 8/1986 | Walter |
| 4,647,452 A | 3/1987 | Ritchey et al. |
| 4,652,444 A * | 3/1987 | Maurer ........................ 424/49 |
| 4,654,213 A | 3/1987 | Ramirez et al. |
| 4,661,354 A | 4/1987 | Finnerty |
| 4,665,054 A | 5/1987 | Pickart |
| 4,678,664 A | 7/1987 | Schmolka |
| 4,683,133 A | 7/1987 | Southard |
| 4,708,864 A * | 11/1987 | Maurer ........................ 424/49 |
| 4,713,242 A | 12/1987 | Trenzeluk |
| 4,760,051 A | 7/1988 | Pickart |
| 4,762,715 A | 8/1988 | Lukas et al. |
| 4,767,753 A | 8/1988 | Pickart |
| 4,810,693 A | 3/1989 | Pickart |
| 4,816,254 A | 3/1989 | Moss |
| 4,847,083 A | 7/1989 | Clark |
| 4,849,211 A | 7/1989 | Schrauzer |
| 4,855,138 A | 8/1989 | Trenzeluk |
| 4,863,987 A | 9/1989 | Hoshino et al. |
| 4,874,361 A | 10/1989 | Obagi |
| 4,877,770 A | 10/1989 | Pickart |
| 4,895,727 A | 1/1990 | Allen |
| 4,911,932 A | 3/1990 | Clum et al. |
| 4,937,230 A | 6/1990 | Pickart |
| 4,938,969 A | 7/1990 | Schinitsky et al. |
| 4,956,354 A | 9/1990 | Gutierrez |
| RE33,512 E | 1/1991 | Ramirez et al. |
| 4,992,259 A | 2/1991 | Schiraldi et al. |
| 5,000,944 A | 3/1991 | Prencipe et al. |
| 5,023,237 A | 6/1991 | Pickart |
| 5,059,588 A | 10/1991 | Pickart |
| 5,075,469 A | 12/1991 | Chevion |
| 5,079,010 A | 1/1992 | Natterer |
| 5,091,171 A | 2/1992 | Yu et al. |
| 5,091,193 A | 2/1992 | Enjolras et al. |
| 5,093,099 A | 3/1992 | Haishi et al. |
| 5,104,644 A | 4/1992 | Douglas |
| 5,118,665 A | 6/1992 | Pickart |
| 5,120,831 A | 6/1992 | Pickart |
| 5,135,913 A | 8/1992 | Pickart |
| 5,145,838 A | 9/1992 | Pickart |
| 5,154,932 A | 10/1992 | Burba, III et al. |
| 5,164,367 A | 11/1992 | Pickart |
| 5,165,914 A | 11/1992 | Vlock |
| 5,166,176 A | 11/1992 | Obagi et al. |
| 5,174,990 A | 12/1992 | Douglas |

| Patent | Date | Name |
|---|---|---|
| 5,177,061 A | 1/1993 | Pickart |
| 5,209,932 A | 5/1993 | Nichols |
| 5,214,032 A | 5/1993 | Pickart |
| 5,227,156 A | 7/1993 | Wiese |
| 5,232,691 A | 8/1993 | Lemole |
| 5,240,696 A | 8/1993 | Van Der Ouderaa et al. |
| 5,244,651 A | 9/1993 | Kayane et al. |
| 5,258,183 A | 11/1993 | Grimberg |
| 5,310,546 A | 5/1994 | Douglas |
| 5,330,748 A | 7/1994 | Winston et al. |
| 5,330,749 A | 7/1994 | Giacin et al. |
| 5,348,943 A | 9/1994 | Pickart |
| 5,352,438 A | 10/1994 | N'Guyen et al. |
| 5,382,431 A | 1/1995 | Pickart |
| 5,385,727 A | 1/1995 | Winston et al. |
| 5,401,730 A | 3/1995 | Sauvage et al. |
| 5,424,077 A | 6/1995 | Lajoie |
| 5,439,863 A | 8/1995 | Bottcher et al. |
| 5,455,023 A | 10/1995 | Giacin et al. |
| 5,466,470 A | 11/1995 | Lajoie |
| 5,480,975 A | 1/1996 | Goldberg et al. |
| 5,482,720 A | 1/1996 | Murphy et al. |
| 5,484,597 A | 1/1996 | Slavtcheff et al. |
| 5,496,539 A * | 3/1996 | Mobley et al. ............... 424/49 |
| 5,500,448 A | 3/1996 | Cummins et al. |
| 5,547,676 A * | 8/1996 | Rocher et al. ............... 424/401 |
| 5,550,183 A | 8/1996 | Pickart |
| 5,552,147 A | 9/1996 | Znaiden et al. |
| 5,554,375 A | 9/1996 | Pickart |
| 5,554,647 A | 9/1996 | Perricone |
| 5,582,817 A * | 12/1996 | Otsu et al. ............... 424/59 |
| 5,597,550 A | 1/1997 | Mo |
| 5,597,552 A | 1/1997 | Herms et al. |
| 5,616,313 A | 4/1997 | Williams et al. |
| 5,622,724 A | 4/1997 | Bryce-Smith |
| 5,624,675 A | 4/1997 | Kelly |
| 5,631,013 A | 5/1997 | Bergmann et al. |
| 5,632,972 A | 5/1997 | Williams et al. |
| 5,645,840 A | 7/1997 | Lajoie et al. |
| 5,663,213 A | 9/1997 | Jones et al. |
| 5,686,083 A | 11/1997 | Chamness |
| 5,688,492 A | 11/1997 | Galley et al. |
| 5,690,967 A | 11/1997 | Yu et al. |
| 5,696,169 A | 12/1997 | Otsu et al. |
| 5,698,184 A | 12/1997 | Pickart |
| 5,707,609 A | 1/1998 | Mo |
| 5,708,023 A | 1/1998 | Modak et al. |
| 5,728,404 A | 3/1998 | Von Rheinbaben et al. |
| 5,747,005 A | 5/1998 | Barels et al. |
| 5,753,637 A | 5/1998 | Fried |
| 5,762,945 A | 6/1998 | Ashley et al. |
| 5,780,020 A | 7/1998 | Peterson et al. |
| 5,795,574 A | 8/1998 | Breton et al. |
| 5,798,121 A | 8/1998 | Cauwet et al. |
| 5,827,884 A | 10/1998 | Obagi et al. |
| 5,837,270 A | 11/1998 | Burgess |
| 5,855,873 A | 1/1999 | Yam |
| 5,858,335 A | 1/1999 | Lucas et al. |
| 5,858,371 A | 1/1999 | Singh et al. |
| 5,858,993 A * | 1/1999 | Pickart ............... 514/60 |
| 5,861,143 A | 1/1999 | Peterson et al. |
| 5,861,144 A | 1/1999 | Peterson et al. |
| 5,861,145 A | 1/1999 | Lucas et al. |
| 5,861,146 A | 1/1999 | Peterson et al. |
| 5,861,147 A | 1/1999 | Dodd et al. |
| 5,871,718 A | 2/1999 | Lucas et al. |
| 5,871,719 A | 2/1999 | Lucas et al. |
| 5,874,067 A | 2/1999 | Lucas et al. |
| 5,874,070 A | 2/1999 | Trinh et al. |
| 5,879,666 A | 3/1999 | Lucas et al. |
| 5,882,638 A | 3/1999 | Dodd et al. |
| 5,886,184 A | 3/1999 | Dolling et al. |
| 5,888,515 A | 3/1999 | Albert et al. |
| 5,888,522 A | 3/1999 | Pickart |
| 5,897,854 A | 4/1999 | Lucas et al. |
| 5,897,855 A | 4/1999 | Trinh et al. |
| 5,897,856 A | 4/1999 | Trinh et al. |
| 5,904,921 A | 5/1999 | Bresson-Rival et al. |
| 5,911,976 A | 6/1999 | Trinh et al. |
| 5,928,631 A | 7/1999 | Lucas et al. |
| 5,928,658 A | 7/1999 | Kishida et al. |
| 5,935,608 A | 8/1999 | Fujikawa et al. |
| 5,942,214 A | 8/1999 | Lucas et al. |
| 5,948,390 A | 9/1999 | Nelson et al. |
| 5,951,990 A | 9/1999 | Ptchelintsev |
| 5,955,067 A | 9/1999 | Oge et al. |
| 5,961,993 A | 10/1999 | Boussouira et al. |
| 5,965,137 A | 10/1999 | Petrus |
| 5,965,610 A | 10/1999 | Modak et al. |
| 5,972,999 A * | 10/1999 | Murad ............... 514/474 |
| 5,980,477 A | 11/1999 | Kelly |
| 5,994,403 A | 11/1999 | Donatiello |
| 6,019,976 A | 2/2000 | Bryant |
| 6,022,565 A | 2/2000 | Albert et al. |
| 6,030,605 A | 2/2000 | D'Ameila et al. |
| 6,037,386 A | 3/2000 | Modak et al. |
| 6,046,178 A | 4/2000 | Silvetti, Sr. |
| 6,060,079 A | 5/2000 | Freeman et al. |
| 6,071,543 A | 6/2000 | Thornfeldt |
| 6,083,490 A | 7/2000 | Ellis et al. |
| 6,086,666 A | 7/2000 | Noguchi et al. |
| 6,103,247 A | 8/2000 | Boussouira et al. |
| 6,103,273 A | 8/2000 | Antoun |
| 6,113,636 A | 9/2000 | Ogle |
| 6,121,254 A | 9/2000 | Saint-Leger |
| 6,123,925 A | 9/2000 | Barry et al. |
| 6,132,743 A | 10/2000 | Kuroda et al. |
| 6,143,318 A | 11/2000 | Gilchrist et al. |
| 6,149,947 A | 11/2000 | Hon et al. |
| 6,183,785 B1 | 2/2001 | Westfall |
| 6,190,407 B1 | 2/2001 | Ogle et al. |
| 6,191,167 B1 | 2/2001 | Yu et al. |
| 6,200,580 B1 | 3/2001 | Horino et al. |
| 6,200,680 B1 | 3/2001 | Takeda et al. |
| 6,217,914 B1 | 4/2001 | Meisner |
| 6,221,403 B1 | 4/2001 | Nesbit |
| 6,224,896 B1 | 5/2001 | Redmond |
| 6,248,370 B1 | 6/2001 | Harris |
| 6,261,574 B1 | 7/2001 | Costello |
| 6,267,782 B1 | 7/2001 | Ogle et al. |
| 6,287,541 B1 | 9/2001 | Creeth et al. |
| 6,303,651 B1 | 10/2001 | Hersh |
| 6,322,588 B1 | 11/2001 | Ogle et al. |
| 6,322,820 B1 | 11/2001 | Simoneau |
| 6,331,567 B1 | 12/2001 | Watson et al. |
| 6,361,800 B1 | 3/2002 | Cooper et al. |
| 6,375,942 B1 | 4/2002 | Rico |
| 6,395,301 B1 | 5/2002 | Cantin |
| 6,416,744 B1 | 7/2002 | Robinson et al. |
| 6,444,699 B2 | 9/2002 | Meisner |
| 6,451,294 B1 | 9/2002 | Simon |
| 6,471,972 B1 | 10/2002 | Bonte et al. |
| 6,475,526 B1 | 11/2002 | Smith |
| 6,517,849 B1 | 2/2003 | Seger et al. |
| 6,521,265 B1 | 2/2003 | Patterson |
| 6,558,710 B1 | 5/2003 | Godfrey |
| 6,579,541 B2 | 6/2003 | Antelman |
| 6,582,684 B1 | 6/2003 | Abrahamson |
| 6,582,710 B2 | 6/2003 | Deckers et al. |
| 6,592,852 B1 | 7/2003 | Ryles et al. |
| 6,599,513 B2 | 7/2003 | Deckers et al. |
| 6,607,716 B1 | 8/2003 | Smith et al. |
| 6,627,178 B1 | 9/2003 | Cawthon |
| 6,660,306 B2 | 12/2003 | Peshoff |
| 6,663,852 B2 | 12/2003 | Simon |
| 6,680,073 B1 | 1/2004 | Tarbet |

| | | |
|---|---|---|
| 6,682,720 B2 | 1/2004 | Ryles et al. |
| 6,696,071 B2 | 2/2004 | Kelly |
| 6,726,919 B2 | 4/2004 | Pace et al. |
| 6,730,309 B2 | 5/2004 | Horino |
| 6,730,329 B1 | 5/2004 | Smith |
| 6,743,416 B2 | 6/2004 | Riedl |
| 6,750,209 B1 | 6/2004 | Hudson et al. |
| 6,773,698 B1 | 8/2004 | Melinte et al. |
| 6,780,439 B2 | 8/2004 | Wilk |
| 6,800,301 B2 | 10/2004 | Smith |
| 6,833,362 B2 | 12/2004 | Bowen, Jr. et al. |
| 6,844,012 B1 | 1/2005 | Forceville et al. |
| 6,849,277 B2 | 2/2005 | Roig |
| 6,855,341 B2 | 2/2005 | Smith |
| 6,858,201 B2 | 2/2005 | Pickart |
| 6,929,800 B2 | 8/2005 | Salman |
| 6,932,976 B2 | 8/2005 | Brooks |
| 6,939,568 B2 | 9/2005 | Burrell et al. |
| 6,942,878 B2 | 9/2005 | Ishii et al. |
| 6,949,248 B2 | 9/2005 | Nishihama |
| 6,949,249 B2 | 9/2005 | Healy et al. |
| 6,964,782 B1 | 11/2005 | Smith et al. |
| 6,979,468 B1 * | 12/2005 | Pollard ........................ 424/643 |
| 6,989,156 B2 | 1/2006 | Gillis |
| 7,008,647 B2 | 3/2006 | Burrell et al. |
| 7,014,870 B1 | 3/2006 | Hon et al. |
| 7,026,308 B1 | 4/2006 | Gavin et al. |
| 7,049,339 B2 | 5/2006 | Thomson |
| 2001/0014356 A1 | 8/2001 | Yoshida et al. |
| 2001/0041193 A1 | 11/2001 | Meisner |
| 2002/0001629 A1 | 1/2002 | Voellmy |
| 2002/0031557 A1 | 3/2002 | Meisner |
| 2002/0114847 A1 | 8/2002 | Peshoff |
| 2002/0182244 A1 | 12/2002 | Jackson |
| 2003/0004564 A1 | 1/2003 | Elkins et al. |
| 2003/0026848 A1 | 2/2003 | Joshi |
| 2003/0035825 A1 | 2/2003 | Shiau et al. |
| 2003/0059484 A1 | 3/2003 | Bonte et al. |
| 2003/0068351 A1 | 4/2003 | Roig |
| 2003/0072819 A1 | 4/2003 | Tao |
| 2003/0077304 A1 | 4/2003 | McCadden |
| 2003/0077332 A1 | 4/2003 | Godfrey |
| 2003/0082219 A1 | 5/2003 | Warren et al. |
| 2003/0082223 A1 | 5/2003 | Healy et al. |
| 2003/0099721 A1 | 5/2003 | Yoshida et al. |
| 2003/0118623 A1 | 6/2003 | De Paoli Ambrosi |
| 2003/0133991 A1 | 7/2003 | Monroe et al. |
| 2003/0138497 A1 | 7/2003 | Sakuma et al. |
| 2003/0161892 A1 | 8/2003 | McFarland |
| 2003/0190371 A1 | 10/2003 | Graaf et al. |
| 2003/0194446 A1 | 10/2003 | Akes et al. |
| 2003/0199488 A1 | 10/2003 | Trotta |
| 2003/0215412 A1 | 11/2003 | Waugh et al. |
| 2003/0215522 A1 | 11/2003 | Johnson et al. |
| 2003/0224023 A1 | 12/2003 | Faryniarz et al. |
| 2003/0224027 A1 | 12/2003 | Faryniarz et al. |
| 2004/0022863 A1 | 2/2004 | Hamtini |
| 2004/0028708 A1 | 2/2004 | Brooks |
| 2004/0033270 A1 | 2/2004 | Kropf et al. |
| 2004/0037910 A1 | 2/2004 | Hon et al. |
| 2004/0058011 A1 | 3/2004 | Petersson |
| 2004/0058015 A1 | 3/2004 | Tao |
| 2004/0062730 A1 | 4/2004 | Kurosawa et al. |
| 2004/0062817 A1 | 4/2004 | Peshoff |
| 2004/0076686 A1 | 4/2004 | Riesinger |
| 2004/0091551 A1 | 5/2004 | Damji |
| 2004/0101541 A1 | 5/2004 | Heffernan et al. |
| 2004/0109902 A1 | 6/2004 | McDonagh et al. |
| 2004/0131700 A1 | 7/2004 | Cifra et al. |
| 2004/0147189 A1 | 7/2004 | Smith et al. |
| 2004/0156875 A1 | 8/2004 | Fabre et al. |
| 2004/0157921 A1 | 8/2004 | Cifra et al. |
| 2004/0170701 A1 | 9/2004 | Carter |
| 2004/0170703 A1 | 9/2004 | Hoekstra et al. |
| 2004/0170712 A1 | 9/2004 | Sadek El Mogy |
| 2004/0175433 A1 | 9/2004 | Thomson |
| 2004/0185015 A1 | 9/2004 | Zhang et al. |
| 2004/0185074 A1 | 9/2004 | Faryniarz et al. |
| 2004/0202689 A1 | 10/2004 | Subramanyan et al. |
| 2004/0220100 A1 | 11/2004 | Waugh et al. |
| 2004/0253321 A1 | 12/2004 | Fechner et al. |
| 2004/0258769 A1 | 12/2004 | Barker et al. |
| 2005/0048010 A1 | 3/2005 | Klis et al. |
| 2005/0069506 A1 | 3/2005 | Katusic et al. |
| 2005/0069588 A1 | 3/2005 | Taal |
| 2005/0074425 A1 | 4/2005 | Waugh et al. |
| 2005/0079229 A1 | 4/2005 | Cawthon |
| 2005/0100571 A1 | 5/2005 | Keyes |
| 2005/0123620 A1 | 6/2005 | Chiou |
| 2005/0136129 A1 | 6/2005 | Verheul-Koot et al. |
| 2005/0175719 A1 | 8/2005 | Sun et al. |
| 2005/0202054 A1 | 9/2005 | Faryniarz et al. |
| 2005/0234239 A1 | 10/2005 | Taillefer et al. |
| 2005/0238730 A1 | 10/2005 | Le Fur et al. |
| 2006/0029682 A1 | 2/2006 | Monroe et al. |
| 2006/0036007 A1 | 2/2006 | Hsieh et al. |
| 2007/0184017 A1 * | 8/2007 | Faryniarz et al. ......... 424/78.37 |
| 2007/0191620 A1 * | 8/2007 | Ramirez et al. ............. 556/114 |
| 2007/0203354 A1 * | 8/2007 | Ramirez et al. ............. 556/114 |
| 2008/0081077 A1 * | 4/2008 | Faryniarz et al. ............ 424/630 |

FOREIGN PATENT DOCUMENTS

WO  WO 2004/039238 A2  5/2004
WO  WO 2004/039238 A3  5/2004

OTHER PUBLICATIONS

Pasán, J., et al., "Malonate-based copper(II) coordination compounds: Ferromagnetic coupling controlled by dicarboxylates", *Polyhedron* 2003, accepted.

Rodríguez-Martín Y., "Alternating cationic-anionic layers in the [MII(H$_2$O)$_6$][Cu$^{II}$(mal)$_2$(H$_2$O)] complexes linked through hydrogen bonds (M=Mn, Co, Ni, Cu and Zn; H$_2$mal=Malonic acid)", *CrystEngComm*, 2002, vol. 4, No. 107, 631.

Hernández-Molina M., "A phase transition in the novel three-dimensional compound [Eu$_2$(mal)$_2$(H$_2$O)$_6$] (H$_2$mal=malonic acid)", *J.Chem.Soc., Dalton Trans.* 2002, vol. 18, 3462.

Rodríguez-Martín, Y., "Structural Versatility of the Malonate Ligand as a Tool for Crystal Engineering in the Design of Molecular Magnets", *Cryst. Eng. Comm.* 2002, vol. 4, No. 87, 522-535.

Rodríguez-Martín, Y., "Combining coordination chemistry and hydrogen bonds: Synthesis, Crystal Structures and thermal behaviour of the complexes [MII(L)(bpy)(H$_2$O)$_n$]·(NO$_3$)$_2$ (M$^{II}$=Cu and Ni, n=1 or 2, L=malonamide, bipy=2,2'-bipyridine)", *J. Coord. Chem.* (2002) in press.

Sanchiz, J., "Ferromagnetic coupling in the malonato-bridged copper(II) chains {[Cu(Im)$_2$(mal)]}$_n$ and {[Cu(2-MeIm)$_2$(mal)]}$_n$ (H$_2$mal=Malonic Acid, Im=imidazole and 2-MeIm=2-methylimidazole)", *New J. Chem.* 2002, vol. 26, 1624.

Rodríguez-Martín, Y., "The flexibility of molecular components as a suitable tool in designing extended magnetic systems", *Cryst. Eng. Comm.* 2002, vol. 4, No. 73, 440-446.

Ruiz-Pérez, C., "Dimensionally controlled hydrogen-bonded nanostructures: Synthesis, structure, thermal and magnetic behaviour of the tris-(chelated)nickel(II) complex [Ni(bipy)$_3$]Cl$_2$·5.5H$_2$O (bipy=2,2'-bipyridine)", *Inorg. Chim. Acta.* 2002, vol. 336, 131-136.

Rodríguez-Martín, Y., "Extended network via hydrogen bond linkages of coordination compounds: Synthesis, crystal structure and thermal behavior of the complexes [MII(L)$_2$(NO$_3$)$_2$] (MII=Cu, Co) and [Ni(L)$_2$(H$_2$O)$_2$]·(NO$_3$)$_2$ (L=malonamide)", *Inorganica Chimica Acta.* vol. 328, 169-178 (2002).

Rodríguez-Martín, Y., "Synthesis, crystal structure and magnetic properties of [Cu(bpym)(mal)(H$_2$O)]·6H$_2$O and [Cu$_2$(bpym)(mal)$_2$(H$_2$O)$_2$]·4H$_2$O (bpym=2,2'-bipyrimidine, H2mal=Malonic Acid)", *Inorganica Chimica Acta.* vol. 326, 20-26 (2001).

Delgado, F., "Alkali-Templated Malonate Copper (II) Complexes", *Acta Cryst*. A61, C358 (2005).

Naumov, P, et al., "The Crystal Structure of Copper (II) Malonate Trihydrate", *CCACAA*, vol. 75, No. 3, 701-711 (2002).

Filippova I.G., "Polymorphism of Coordination Compounds with Malonic Añid", *Moldavian Journal of the Physical Sciences*, 1vol. 1, No. 3, 87-93 (2002).

Tinker, D. et al., "Role of Selected Nutrients in Synthesis, Accumulation, and Chemical Modification of Connective Tissue Proteins", *Physiolgical Reviews*, vol. 65, No. 3, 607-657 (1985).

Philip, B., et al., "Dietary Zinc & Levels of Collagen, Elastin & Carbohydrate Components of Glycoproteins of Aorta, Skin & Cartilage in Rats", *Indian J. Exp. Biol.*, vol. 16, 370-372 (1978).

Homsy, R. et al., "Characterization of Human Skin Fibroblasts Elastase Activity", *J. Invest. Dermatol*, vol. 91, 472-477 (1988).

Chen et al., "Preparation and Kinetics of the Thermal Decomposition of Nanosized $CuC_2O_4$-$ZnC_3O_4$ $2H_2O$", Wuhan University Journal of Natural Sciences, vol. II, No. 3, pp. 667-671, May 2006.

M.A. Gabal, "Kinetics of the Thermal Decomposition of $CuC_2O_4$-$ZnC_2O_4$ Mixture in Air", Thermochimica Acta 402 (2003) pp. 199-208.

Huang Lianrong et al., "Thermal Behavior of Kinetics of the Decomposition of $CuC_2O_4$-$ZnC_2O_4$ $2H_2O$ by Different Preparation Methods", Journal of South-Central University for Nationalities (Nat. Sci. Edition), vol. 23, No. 3, pp. 12-16, Sep. 2004.

\* cited by examiner

CHEMICAL COMPOSITIONS AND METHODS OF MAKING THEM

CROSS REFERENCE TO RELATED APPLICATION

This application claims priority benefit of U.S. Provisional Application No. 60/764,968 filed Feb. 3, 2006 the entire disclosure of which is incorporated herein by this reference.

BACKGROUND

1. Technical Field

The present disclosure relates compositions that contain bimetal complexes. The bimetal complexes can be prepared by reacting a polyfunctional compound with two or more coordination elements.

2. Background of the Invention

Malonic acid is a polyfunctional acid used in many products. The ion form of malonic acid, as well as its esters and salts, are known as malonates. Various copper malonates are known through the extensive use of the malonato ion in crystal engineering to explore the structural chemistry of copper (II) malonate, which exists in several hydrated forms such as copper (II) malonate dihydrate, copper (II) malonate trihydrate, and copper malonate tetrahydrate. Other copper (II) malonate hydrates are also known. However, the study of reaction products of polyfunctional acids and the formation of malonates is problematic in that conditions of synthesis, stoichiometry and temperature should be known and applied in order to synthesize the desired product. For example, the mixture of copper carbonate and malonic acid in a 1:2 molar ratio kept at 5° C. for weeks results in the formation of deep blue copper (II) malonate trihydrate crystals.

It would be desirable to provide compositions containing reaction products of polyfunctional compounds with two or more coordination elements. It would also be desirable to provide malonates having both copper/zinc and/or other metallic constituents.

SUMMARY

Compositions in accordance with the present disclosure contain a bimetal complex. The bimetal complex can be the reaction product of a polyfunctional acid with two or more coordination elements. The coordination elements can be selected from the elements listed in Groups IIIA to VIIIA, Groups IB to IIIB, of periods 4 and 5 and aluminum in Group IIIB, period 3 of The Periodic Table of the Elements.

Methods of making such reaction products are also described. In embodiments, bimetal complexes are made by 1) contacting one or more polyfunctional acids with two or more coordination elements, wherein the molar ratio of polyfunctional acids to two or more coordination elements is at least 3:2; and 2) isolating the reaction product.

In embodiments, copper-zinc malonate complexes are synthesized from malonic acid and copper and zinc constituents. Methods of making copper-zinc dual salts are also described. In embodiments, copper-zinc malonate compositions are made by:

1) contacting malonic acid with one or more bases containing copper and zinc constituents in an aqueous solution, wherein the molar ratio of malonic acid to copper to zinc is about 3:1:1; and 2) recovering the copper-zinc malonate product.

Excess malonic acid in the manufacturing process may drive the formation of copper-zinc malonates which precipitate in the reaction solution.

DETAILED DESCRIPTION OF PREFERRED EMBODIMENTS

The preparation of reaction products of polyfunctional acids with two or more coordination elements and compositions containing such reaction products are described.

The polyfunctional acid can be any compound that contains at least two carboxylic acid groups that may complex with metal cations in solution. Polyfunctional acids are primarily monomeric compositions having two or more carboxylic acid groups. Non-limiting examples of polyfunctional acids include maleic acid, fumaric acid, citraconic acid, itaconic acid, glutaconic acid, phthalic acid, isophthalic acid, terephthalic acid, cyclohexane dicarboxylic acid, succinic acid, adipic acid, sebacic acid, azealic acid, malonic acid, dodecanedioic acid, 1,18-octadecanedioic acid, dimer acids (prepared from a mono-, di- or triunsaturated fatty acid, acid wax, acid anhydride grafted wax, or other suitable polycarboxylic acid reacting compound), alkenyl succinic acids (such as n-dodecenylsuccinic acid, docecylcucinic acid and octadecenylsuccinic acid). The polyfunctional acid can be present in acidic form, anhydride form, salt form, or mixtures thereof.

The polyfunctional acid is reacted with two or more coordination elements. The coordination elements can be chosen from the elements listed in Groups IIIA to VIIIA, Groups IB to IIIB, of periods 4 and 5 and aluminum in Group IIIB, period 3 of The Periodic Table of the Elements. Suitable non-limiting examples of elements listed in group IB of The Periodic Table of Elements include copper, silver, and gold. Suitable non-limiting examples of coordination elements include aluminum, scandium, titanium, vanadium, chromium, manganese, iron, cobalt, nickel, copper, zinc, gallium, yttrium, zirconium, niobium, molybdenum, technetium, ruthenium, rhodium, palladium, silver, cadmium, and indium. Tin may also be used. Those skilled in the are will readily envision suitable compounds for providing the coordination elements in solution.

For example, water soluble salts containing the coordination element may be used. The salts may be organic or inorganic. Suitable water-soluble silver salts include silver nitrate, silver acetate, silver propionate, silver sulfate, silver butyrate, silver isobutyrate, silver benzoate, silver tartrate, silver salicylate, silver malonate, silver succinate and silver lactate. Suitable water-soluble aluminum salts include aluminum potassium sulfate, aluminum chloride, aluminum sodium sulfate, aluminum sodium phosphate, aluminum sulfate, aluminum nitrate, and sodium aluminate. Suitable water-soluble copper salts include copper sulfate, fluoroborate, hydroxide, borate, fluoride, carbonate, oxychloride, formate or acetate. Suitable water-soluble zinc salts include zinc chloride, zinc bromide, zinc iodide, zinc chlorate, zinc bromate, zinc chlorite, zinc perchlorate, zinc sulfate, zinc nitrate, zinc nitrite, zinc borate, zinc metaborate, basic zinc borate, zinc hexafluorosilicate, zinc hypophosphite, zinc glycerophosphate, zinc bichromate, zinc citrate, zinc thionate, zinc dithionate, zinc tetrathionate, zinc pentathionate, zinc thiocyanate, zinc benzoate, zinc acetate, zinc salicylate, zinc picrate, zinc permanganate, zinc hydrogen phosphate, zinc formate, zinc ethylsulfate and zinc phenolsulfonate. Examples of suitable water soluble nickel salts that may be used include nickel sulfate hexahydrate and nickel chloride hexahydrate. It should be understood that the listed salts are only a small portion of the salts suitable for use in accordance with the present disclosure. For example, inorganic salts are suitable provided that they provide coordination element cations when placed in an aqueous solution. Thus, the foregoing list of salts should be considered a non-limiting, illustrative list.

For carrying out the process, a reaction solution can be prepared by mixing the various ingredients in water. Water in the mixture may advantageously be added in limited amounts sufficient to allow the reaction product to precipitate from solution upon formation. Accordingly, the reaction mixture is not so dilute as to prevent product precipitate formation. Where necessary, mixing and heating can be used to bring the reactants to 40-100° C. in order to solubilize the reactants. As a result, reactant solubility may be enhanced through energy input such as microwave heating or addition of boiling water. The input of the energy may take place through any instrument capable of heating the aqueous reaction mixture. The reaction products formed in solution may be immediately separated so that their production can take place in a continuous process. Where a short reaction time and rapid crystallization of the reaction product occur, the conversion may be carried out continuously, and the recovery of the resultant solid product may take place by any conventional manner such as filtering, centrifugation, or sedimentation.

The polyfunctional acid is present in the reaction mixture in amounts that will contact metal cations in an aqueous solution. Suitable amounts of polyfunctional acid also include excess amounts in relation to the amount of metal cations. In embodiments, polyfunctional acid is present in a 3:1:1 molar ratio in relation to the metal constituents. In embodiments, the polyfunctional acid is malonic acid which can be present in acidic form, salt form, or mixtures thereof.

In embodiments, the process parameters are especially advantageous if the polyfunctional acid is added to excess in comparison to the metal counter cation constituents. Depending on the desired complex, the latter are added so that the molar ratio of polyfunctional acid to metal ions is approximately 3:2.

In embodiments, the coordination elements may be present as one or more ionic compounds formed by joining one or more independent coordination element molecules or ions of a first type and coordination element molecules or ions of a second type to a central unit by ionic bonds. For example, the reaction product may be in the form of a trinuclear cation, where structurally independent coordination element hydrates are bridged by a central unit. However, various coordination modes are possible depending on the source of the coordination elements and synthesis conditions. In embodiments, the central unit may be a multi-membered ring such as eight-membered ring, six-membered ring, and four-membered metalocycle for bridging or chelating functions between the coordination element constituents. Accordingly, the crystal structures of the reaction products can be very diverse, from ionic to three-dimensional polymers. In embodiments, the reaction products are present in several hydrate, and polymorphic forms.

In embodiments, suitable reaction products can be non-toxic bimetal complexes that include copper, zinc, aluminum and/or silver constituents. Such copper, zinc, aluminum and/or silver reaction products include, but are not limited to water soluble compounds that contain copper, zinc, aluminum and/or silver. Non-limiting examples of water-soluble bimetal complexes include copper-zinc citrate, copper-silver citrate, silver-zinc citrate, copper-zinc oxalate, copper-silver oxalate, silver-zinc oxalate, copper-zinc tartarate, copper-silver tartarate, silver-zinc tartarate, copper-zinc malate, copper-silver malate, silver-zinc malate, copper-zinc succinate, copper-silver succinate, silver-zinc succinate, copper-zinc malonate, copper-silver malonate, silver-zinc malonate, copper-zinc maleate, copper-silver maleate, silver-zinc maleate, copper-zinc aspartate, copper-silver aspartate, silver-zinc aspartate, copper-zinc glutamate, copper-silver glutamate, silver-zinc glutamate, copper-zinc glutarate, copper-silver glutarate, silver-zinc glutarate, copper-zinc fumarate, copper-silver fumarate, silver-zinc fumarate, copper-zinc glucarate, copper-silver glucarate, silver-zinc glucarate, copper-zinc polyacrylic acid, copper-silver polyacrylic acid, silver-zinc polyacrylic acid, and combinations thereof. In embodiments, copper, zinc, aluminum and silver salts of organic multi carboxylic acids are suitable for use in accordance with the present disclosure. In embodiments, suitable salts can be doped such that the unit cell of the salt has zinc or silver constituents dispersed therein. Such zinc or silver constituents may either substitute another metallic constituent or fill a preexisting void in the unit cell.

In embodiments, suitable reaction products can be copper salts having zinc or silver constituents therein. For example, zinc or silver may either substitute a copper constituent or fill a preexisting void in the copper salt's unit cell. Suitable non-limiting examples of copper salts which may be used to form bimetallic complexes include copper (II) malonate and any hydrated form thereof such as copper (II) malonate dihydrate, copper (II) malonate trihydrate, and copper malonate tetrahydrate. Other suitable non-limiting examples of suitable copper salt active ingredients include copper citrate, copper oxalate, copper tartarate, copper malate, copper succinate, copper malonate, copper maleate, copper aspartate, copper glutamate, copper glutarate, copper fumarate, copper glucarate, copper polyacrylic acid, and combinations thereof. In embodiments, suitable copper salts can be doped such that the unit cell of the salt has zinc or silver constituents dispersed therein. Such zinc or silver constituents may either substitute a copper constituent or fill a preexisting void in the unit cell.

Cu/Zn Malonate Preferred Embodiments

In embodiments, malonic acid may be reacted with salts containing copper and zinc constituents in an aqueous solution. It has been found that where the malonic acid, copper and zinc constituents are present in at least about a 3:1:1 molar ratio, copper-zinc malonates may be produced in good yield and high crystalline purity.

Malonic acid refers to 1,3-propanedioic acid, a dicarboxylic acid with structure $CH_2(COOH)_2$ or:

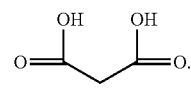

The ion form of malonic acid, as well as its esters and salts, are known as malonates. For example, diethyl malonate is ethyl ester of malonic acid. As used herein, the term copper-zinc malonate applies to any salt substances formed from malonic acid having copper and zinc constituents.

Suitable ingredients for the formation of copper-zinc malonates include malonic acid, one or more bases of copper and zinc, and water. In an aqueous reaction solution, suitable salt forms provide copper and zinc cations capable of bonding to malonate anions. Other suitable ingredients for the formation of copper-zinc malonates will include the replacement of bases of copper and zinc with the metallic form of copper and zinc. The elemental form of copper and zinc are known as copper and zinc metals and will be dissolved in the acidic water media as they react with malonic acid.

One or more salts containing copper and zinc constituents are present in amounts that will contact malonic acid in an aqueous solution. Suitable salts for making copper-zinc malonate compositions in accordance with this disclosure include metal salts containing complex-forming metal ions of copper and/or zinc. Non-limiting examples of suitable metal salts are copper (I) and (II) salts such as copper chloride, copper bromide, copper fluoride, copper nitrate, copper fluoroborate, copper sulfate, copper acetate, copper trifluoro acetate, copper stearate, copper octoate, copper methacrylate, copper malonate, copper benzoate; zinc salts such as zinc bromide, zinc chromate, zinc chloride, zinc stearate, zinc octoate, and zinc ethylhexoate. In embodiments, the aqueous solution may include one or more metallic salts, such as cupric carbonate ($CuCO_3 \cdot Cu(OH)_2$), zinc carbonate ($3Zn(OH)_2 \cdot 2ZnCO_3$), metallic copper, metallic zinc and combinations thereof. Basic salts such as basic zinc salts, basic copper salts, and combinations thereof are also suitable for use in accordance with the present disclosure. In embodiments, suitable metal basic salts are: copper (I) and (II) salts such as copper carbonate, copper oxide, and copper hydroxide; and zinc salts such as zinc carbonate, zinc oxide, and zinc hydroxide.

It should be understood that the listed salts are only a small portion of the salts suitable for use in accordance with the present disclosure. For example, inorganic salts are suitable provided that they provide copper and zinc cations when placed in an aqueous solution. Thus, the foregoing list of salts should be considered a non-limiting, illustrative list.

For carrying out the process, the reaction solution can be prepared by mixing the various ingredients in water where malonic acid and the salts may ionize and become more reactive. Water in the mixture is added in limited amounts sufficient to allow copper-zinc malonates to precipitate from solution upon formation. Accordingly, the reaction mixture is not so dilute as to prevent product precipitate formation. Where copper and zinc salts in the reaction mixture are insoluble and form dispersions (such as at cooler temperatures), mixing and heating steps can be applied to bring the reactants to 40-100° C. in order to solubilize the reactants. As a result, reactant solubility may be enhanced through energy input such as microwave heating or addition of boiling water dissolver. The input of the energy may take place through any instrument capable of heating the aqueous reaction mixture. The copper-zinc malonate complexes formed in solution may be immediately separated so that their production can take place in a continuous process. Due to the short reaction time and the rapid crystallization of the copper-zinc malonate product, the conversion may be carried out continuously, and the recovery of the resultant solid product may take place by any conventional manner such as filtering, centrifugation, or sedimentation.

In the production of the reaction mixture, the concentration of the polyfunctional compound and that of the copper and zinc constituents may be pre-selected so that the total concentration of product formed exceeds the solubility equilibrium. This will result in product precipitating from solution in solid form for easy collection.

In embodiments, the final composition may be a deep blue crystal having good yield and substantial crystalline purity. Suitable copper-zinc malonate forms in accordance with the present disclosure include any salt formed from the neutralization of malonic acid by one or more copper containing molecules and one or more zinc containing molecules. Illustrative examples include salt formed by the neutralization of malonic acid by cupric carbonate ($CuCO_3 \cdot Cu(OH)_2$), and zinc carbonate ($3Zn(OH)_2 \cdot 2ZnCO_3$) in an aqueous solution. Here copper may be added first, followed by zinc in order to obtain the salts of the present disclosure.

In embodiments, the copper-zinc malonates may be one or more ionic compounds formed by joining one or more independent copper molecules or ions and one or more independent zinc molecules or ions to a central unit by ionic bonds. For example, the copper-zinc malonate may be in the form of a trinuclear cation, where structurally independent copper and zinc hydrates are bridged by a central unit such as an octahedral diaquadimalonatocopper (II) unit. However, various coordination modes are possible depending on the source of the copper and zinc and synthesis conditions. In embodiments, the central unit malonate ion may be a multi-membered ring such as eight-membered ring, six-membered ring, and four-membered metalocycle for bridging or chelating functions between the copper and zinc constituents. Accordingly, the crystal structures of copper-zinc malonates can be very diverse, from ionic to three-dimensional polymers. In embodiments, the copper-zinc malonates can be found in several hydrate, and polymorphic forms.

In embodiments, the process parameters are especially advantageous if the polyfunctional compound is added to excess in comparison to the metal counter cation constituents. Depending on the desired complex, the latter are added so that the molar ratio of polyfunctional compound to metal ions is approximately 3:2.

Embodiments of Compositions Containing the Reaction Products

In embodiments, the resulting reaction products may serve as active ingredients in compositions suitable for contact with a subject. Such active ingredients may be combined with numerous ingredients to form products of numerous chemical applications, such as catalytical agents, crosslinking of polymers, superconducting electrical materials, pharmaceutical drugs, food supplements, etc. The active ingredients in suitable toxicological compositions can be applied to the skin, or other tissues of humans or other mammals. Such products may include a dermatologically or pharmaceutically acceptable carrier, vehicle or medium, for example, a carrier, vehicle or medium that is compatible with the tissues to which they will be applied. The term "dermatologically or pharmaceutically acceptable," as used herein, means that the compositions or components thereof so described are suitable for use in contact with these tissues or for use in patients in general without undue toxicity, incompatibility, instability, allergic response, and the like. In embodiments, compositions in accordance with the present disclosure can contain any ingredient conventionally used in cosmetics and/or dermatology. In embodiments, active ingredients may be formulated to provide crystals in solution, as well as solid forms.

In embodiments, products containing a reaction product in accordance with the present disclosure as an active ingredient can be in the form of solutions, emulsions (including microemulsions), suspensions, creams, lotions, gels, powders, or other typical solid or liquid compositions used for treatment of age related skin conditions. Such compositions may contain, in addition to the reaction product in accordance with this disclosure, other ingredients typically used in such products, such as antimicrobials, moisturizers and hydration agents, penetration agents, preservatives, emulsifiers, natural or synthetic oils, solvents, surfactants, detergents, gelling agents, emollients, antioxidants, fragrances, fillers, thickeners, waxes, odor absorbers, dyestuffs, coloring agents, powders, viscosity-controlling agents and water, and optionally including anesthetics, anti-itch actives, botanical extracts, conditioning agents, darkening or lightening agents, glitter, humectants, mica, minerals, polyphenols, silicones or derivatives thereof, sunblocks, vitamins, and phytomedicinals.

As an illustrative example, products can be formulated to contain copper-zinc malonate in amounts from about 0.001 to about 5% by weight of the total composition. In embodiments, products can be formulated to contain copper-zinc malonate in an amount from about 0.05 to about 1.0% by weight of the total composition. In other embodiments, the amount of copper-zinc malonate is from about 0.1 to about 0.5% by weight of the total composition. Here, the copper-zinc malonate present may be in a pharmaceutically acceptable salt form. Other active ingredients may be provided in the formulations at the same concentrations.

In embodiments, compositions in accordance with the present disclosure can be topically applied to skin in need of improvement such as the reduction or elimination of an undesirable dermatological condition. As used herein the word "treat," "treating" or "treatment" refers to using the actives or compositions of the present disclosure prophylactically to prevent outbreaks of undesirable dermatological conditions, or therapeutically to ameliorate an existing dermatological condition, and/or extend the duration of the aesthetic benefit of a skin procedure. A number of different treatments are now possible, which reduce and/or eliminate undesirable skin conditions.

As used herein "undesirable skin condition" refers to any skin condition that may require treatment of any sort, including skin having one or more undesirable appearances and/or disagreeable tactile sensations. The term further refers to any cosmetically undesirable skin condition, as well as any undesirable diseased or damaged skin condition.

Non-limiting examples of undesirable skin conditions which can be treated with the topical application of compositions in accordance with the present disclosure include: acne vulgaris (pimples); atopic dermatitis; birthmarks; cafe-au-laits spots; common benign skin tumors or growths; common diseases of the nail such as nail infections caused by bacteria, fungi, yeast and/or virus; paronychia; nail disorder due to skin disease such as psoriasis, and/or nail injury; common skin conditions around the eyes such as eyelid contact dermatitis, atopic dermatitis, bacterial skin infection (impetigo or conjunctivitis), xanthelasma, syringoma, skin tags, milia, Naevus, and/or portwine stains; common skin condition associated with housework such as irritant contact dermatitis, allergic contact dermatitis, contact urticaria, fungal infections, paronychia, and/or viral warts; common diseases of the scalp such as seborrhoeic dermatitis, psoriasis of the scalp, lichen planus, discoid lupus erythematosus (DLE), alopecia greata, seborrhoeic keratoses (seborrhoeic warts, age spots), solar keratoses, angiosarcoma, fungal infection (ringworm, tinea Capitis), bacteria infections of the hair follicles (folliculitis, boils), and/or shingles (Herpes Zoster); common diseases in children such as atopic dermatitis, atopic eczema, discoid eczema, pityriasis alba, vitiligo, and/or alopecia greata; common diseases of the mouth and lips such as oral candidiasis, oral leukoplakia, apthous ulcers, and/or oral lichen planus; common skin problems in elderly such as appearance and texture changes, senile purpura, xerosis/asteatotic eczema, skin Infections/infestations, pigmentary changes, blistering disorders, non-cancerous skin growths, cancerous skin growths, adverse drug reaction, and/or stasis dermatitis; common viral warts; contact allergy; diaper candidiasis, drug allergy, folliculitis; freckles; fungal infections of the skin such as white spot, athlete's foot, jock itch, and/or moniliasis/candidiasis; guttate hypomelanosis; hair loss; hand eczema; impetigo; lines, crow's feet, wrinkles, etc.; melasma; molluscum contagiosum; occupational skin disease such as irritation and/or allergy; post-Inflammatory pigmentation; psoriasis; rosacea; shingles; skin cancers; skin diseases in diabetes mellitus; skin diseases in pregnancy; skin disorders caused by cosmetics such as irritant contact dermatitis and/or allergic contact dermatitis, cosmetic induced pimples (acne), sunscreens allergy, and/or special cosmetic allergies, solar lentigenes; tinea capitis; viral warts; vitiligo; and combinations of these undesirable skin conditions.

In embodiments, compositions in accordance with the present disclosure are suitable for treating diseased skin, or any condition which can result from the excessive amount of pathogens such as fungi, viruses, and or bacterium affecting the skin in any way.

In embodiments, an undesirable skin condition is skin that has a rough texture or uneven appearance such as psoriasis, bumps, razor burns, and/or patches.

The particular active ingredient or ingredients employed, and the concentration in the compositions, generally depends on the purpose for which the composition is to be applied. For example, the dosage and frequency of application can vary depending upon the type and severity of the skin condition.

Treatments in accordance with the present disclosure contact skin with one or more active ingredients such as those containing copper, zinc and/or silver in an effective amount to improve the undesirable skin conditions. In embodiments, patients are treated by topically applying to skin suffering a condition, one or more copper-zinc malonates. In embodiments, patients are treated by topically applying to skin suffering from a condition, one or more salts in accordance with the present disclosure. The active ingredient is applied until the treatment goals are obtained. However, the duration of the treatment can very depending on the severity of the condition. For example, treatments can last several weeks to months depending on whether the goal of treatment is to reduce or eliminate the skin condition.

In treatment embodiments, the compositions and methods in accordance with the present disclosure can be combined with other skin treatment systems. For example, the bimetallic salt complexes and be applied to skin in combination with skin treatment systems such as the Obagi NuDerm® skin treatment system and related Obagi skin care products from O.M.P. Inc. of Long Beach Calif. More specifically copper-zinc malonate compositions can be combined with the Obagi Nuderm® skin treatment system in order to promote the beneficial affects of that system. The active ingredients and formulations in accordance with the present disclosure may either be incorporated into other product formulations, or applied to the skin before, after, and/or during other skin treatments.

In embodiments, the compositions may contain any active ingredient or be formulated and applied as described in commonly owned U.S. patent application entitled *Anti-aging Treatment Using Copper-Zinc Compositions* (U.S. Ser. No. 11/452,642 filed Jun. 14, 2006) herein incorporated by reference in its entirety.

The following non-limiting examples further illustrate compositions and methods in accordance with this disclosure.

EXAMPLE 1

Example 1 below shows suitable ingredients of a reaction mixture for forming copper-zinc malonates in accordance with the present disclosure.

| Ingredient | Amount |
| --- | --- |
| Malonic acid | 1.8 g |
| cupric carbonate | 0.632 g |
| zinc carbonate | 0.626 g |
| Water | 100 ml |

EXAMPLE 2

1.8 g of malonic acid ($CH_2(COOH)_2$) was combined with 0.632 grams of cupric carbonate ($CuCO_3.Cu(OH)_2$), 0.626 g of zinc carbonate ($3Zn(OH)_2.2ZnCO_3$), and 100 ml of water to form a dispersion. The solution was heated until the reactants went into solution. Well-defined deep-blue crystals precipitated and were separated from the aqueous solution of malonic acid, cupric carbonate, and zinc carbonate (3:1:1 molar ratio) that had been kept at room temperature. Duel salt was formed by replacing acid groups with copper and zinc cations in the same molecule. The deep blue crystals were found to have a melting point of about 210° C.

Sample prepared as per ASTM-D-1971-95 (herein incorporated by reference in its entirety) and analyzed by method 6010 (I.C.P.) (herein incorporated by reference in its entirety) showed 16.5% copper and 12.4% zinc.

EXAMPLE 3

1.8 g of malonic acid ($CH_2(COOH)_2$) was combined with 0.632 grams of cupric carbonate ($CuCO_3.Cu(OH)_2$), 0.626 g of zinc carbonate ($3Zn(OH)_2.2ZnCO_3$), and 100 ml of boiling water. Well-defined deep-blue crystals were separated from the aqueous solution of malonic acid, cupric carbonate, and zinc carbonate (3:1:1 molar ratio) that had been kept at room temperature for 1 week.

EXAMPLE 4

3 moles of malonic acid is thoroughly mixed with 1 mole of copper as cupric carbonate and 1 mole of zinc as zinc carbonate in a stirred tank reactor containing 100 ml of heated water (approximately 95-100° C.). After a short reaction time, copper-zinc malonate precipitates out of solution with a high yield. A filtration step is used to isolate the complex as a powder. Deep blue crystals are obtained having a melting point of about 210° C.

EXAMPLE 5

In embodiments, copper-zinc malonate formulations have the following make-up:

| COMPONENT | % BY WEIGHT |
| --- | --- |
| Copper-zinc malonate* (Active ingredient) | 0.1% |

-continued

| COMPONENT | % BY WEIGHT |
| --- | --- |
| Glycerine | 3.0% |
| Propylene Glycol | 25.0% |
| Distilled Water | 71.9% |

EXAMPLE 6

A 72 year old woman is suffering from wrinkling on her face. The composition of example 5 suitable for treatment of skin containing an effective amount of copper-zinc malonate active ingredient is routinely applied to her face twice daily. Wrinkling is reduced or eliminated.

While several embodiments of the disclosure have been described, it is not intended that the disclosure be limited thereto, as it is intended that the disclosure be as broad in scope as the art will allow and that the specification be read likewise. Therefore, the above description should not be construed as limiting, but merely as exemplifications of embodiments. Those skilled in the art will envision other modifications within the scope and spirit of the claims appended hereto.

What is claimed is:

1. A composition comprising
  a pharmaceutically or dermatologically acceptable carrier; and
  a chelate formed by a polyfunctional carboxylic acid with basic salts of two or more coordination elements selected from one or more of copper, silver, gold, aluminum, scandium, titanium, vanadium, chromium, manganese, iron, cobalt, nickel, copper, zinc, gallium, yttrium, zirconium, niobium, molybdenum, technetium, ruthenium, rhodium, palladium, silver, cadmium, and indium, wherein the chelate includes two or more coordination elements are joined to a central unit derived from the polyfunctional carboxylic acid.

2. A composition as in claim 1 wherein the coordination elements are Cu and Zinc.

3. A composition as in claim 1 wherein the polyfunctional acid is malonic acid.

4. A malonate composition comprising:
  one or more copper molecules;
  one or more zinc molecules;
  a central malonate unit, wherein the central malonate unit bridges the one or more copper molecules and one or more zinc molecules by coordinate bonding; and
  a pharmaceutically or dermatologically acceptable carrier.

5. The malonate composition of claim 4 wherein the one or more copper molecules is a tetraaquacopper (II) square.

6. The malonate composition of claim 4 wherein the one or more zinc molecules is a tetraaquazinc square.

7. The malonate composition of claim 4 wherein the central unit is an octahedral diaquadimalonatocopper (II) unit.

* * * * *